US00PP32338P3

(12) United States Plant Patent
Danziger

(10) Patent No.: US PP32,338 P3
(45) Date of Patent: Oct. 13, 2020

(54) ***GAURA* PLANT NAMED 'DGASTEFDR'**

(50) Latin Name: *Gaura lindheimeri*
Varietal Denomination: DGASTEFDR

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/602,188

(22) Filed: Aug. 22, 2019

(65) Prior Publication Data

US 2020/0068770 P1 Feb. 27, 2020

(51) Int. Cl.
*A01H 5/02* (2018.01)
*A01H 6/00* (2018.01)

(52) U.S. Cl.
USPC ..... Plt./432
CPC ..... *A01H 6/00* (2018.05); *A01H 5/02* (2013.01)

(58) Field of Classification Search
USPC ..... Plt./432
CPC ..... A01H 5/02; A01H 6/00
See application file for complete search history.

*Primary Examiner* — Keith O. Robinson
(74) *Attorney, Agent, or Firm* — Cassandra Bright

(57) ABSTRACT

A new and distinct cultivar of *Gaura* plant named 'DGASTEFDR' is disclosed, characterized by good branching, good flower coverage, and a semi-upright, compact habit. Flower color is dark pink. The new variety is a *Gaura*, normally produced as an outdoor garden or container plant.

2 Drawing Sheets

Figure 1:
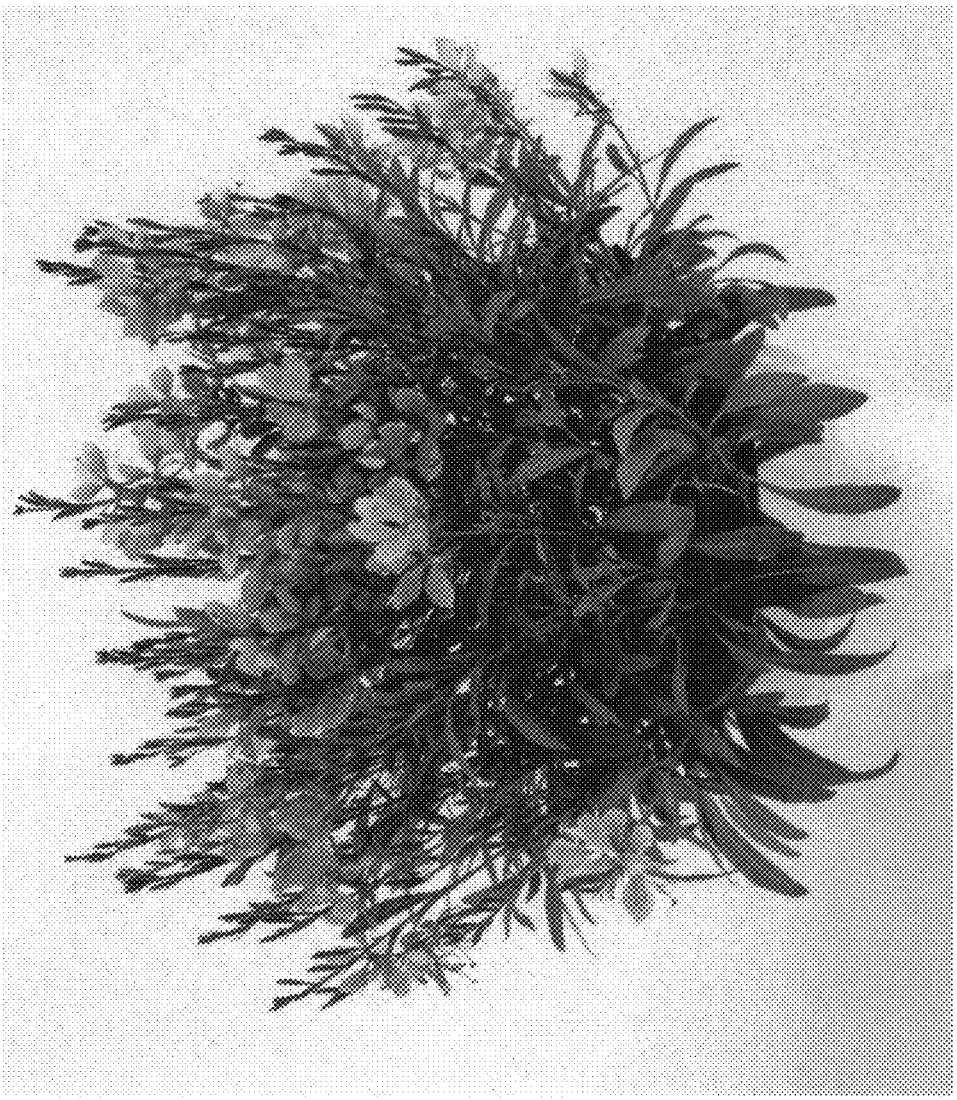

Latin name of the genus and species: *Gaura lindheimeri*. Variety denomination: 'DGASTEFDR'.

BACKGROUND OF THE INVENTION

The new *Gaura* cultivar is a product of an open pollination breeding program conducted by the inventor, Gavriel Danziger in Moshav Mishmar Hashiva, Israel. The objective of the breeding program was to produce new *Gaura* varieties. The open-pollination resulting in this new variety was made during January of 2013.

The seed parent is the unpatented, propriety variety referred to as *Gaura* 'GO-12-220'. The pollen parent is unknown, as it was an open-pollination breeding program. The new variety was discovered in July 2015 by the inventor in a group of seedlings resulting from the crossing, in a greenhouse in Moshav Mishmar Hashiva, Israel. Date of first sale was Sep. 30, 2018, occurring in the United States. This sale was made directly by the inventor or one who obtained the claimed invention directly or indirectly from the inventor. This sale and all public disclosures made between Sep. 30, 2018 and the filing of this application fall within the exception allowed under 102(b)(1).

Asexual reproduction of the new cultivar 'DGASTEFDR' by vegetative cuttings was first performed during July of 2015, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DGASTEFDR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGASTEFDR'. These characteristics in combination distinguish 'DGASTEFDR' as a new and distinct *Gaura* cultivar:

1. Very good branching.
2. Abundant flowering covering most of plant.
3. Semi-upright habit.
4. Compact, medium sized plant.
5. Dark pink flowers.

PARENT COMPARISON

Plants of the new cultivar 'DGASTEFDR' are similar to plants of the seed parent in most horticultural characteristics, however, plants of the new cultivar 'DGASTEFDR' differ in the following;

1. The new variety has darker pink flowers than the seed parent variety.
2. The new variety has longer branches than the seed parent variety.
3. The new variety has darker foliage than the seed parent variety.

COMMERCIAL COMPARISON

Plants of the new cultivar 'DGASTEFDR' can be compared to the unpatented commercial variety *Gaura* 'Belleza Dark Pink'. These varieties are similar in most horticultural characteristics; however, 'DGASTEFDR' differs in the following:

1. The new variety has brighter pink flowers than this comparator.
2. The new variety has brighter green foliage than this comparator.

Plants of the new cultivar 'DGASTEFDR' can also be compared to the unpatented commercial variety *Gaura*

'Gambit Rose'. These varieties are similar in most horticultural characteristics; however, 'DGASTEFDR' differs in the following:

1. The new variety has more branches than this comparator.
2. The new variety has a different habit than this comparator.
3. The new variety has brighter foliage than this comparator.

BRIEF DESCRIPTION OF THE PHOTOGRAPHS

The accompanying photograph in FIG. 1 illustrates in full color a typical plant of 'DGASTEFDR' grown in a greenhouse, in Moshav Mishmar Hashiva, Israel.

Figure 2:
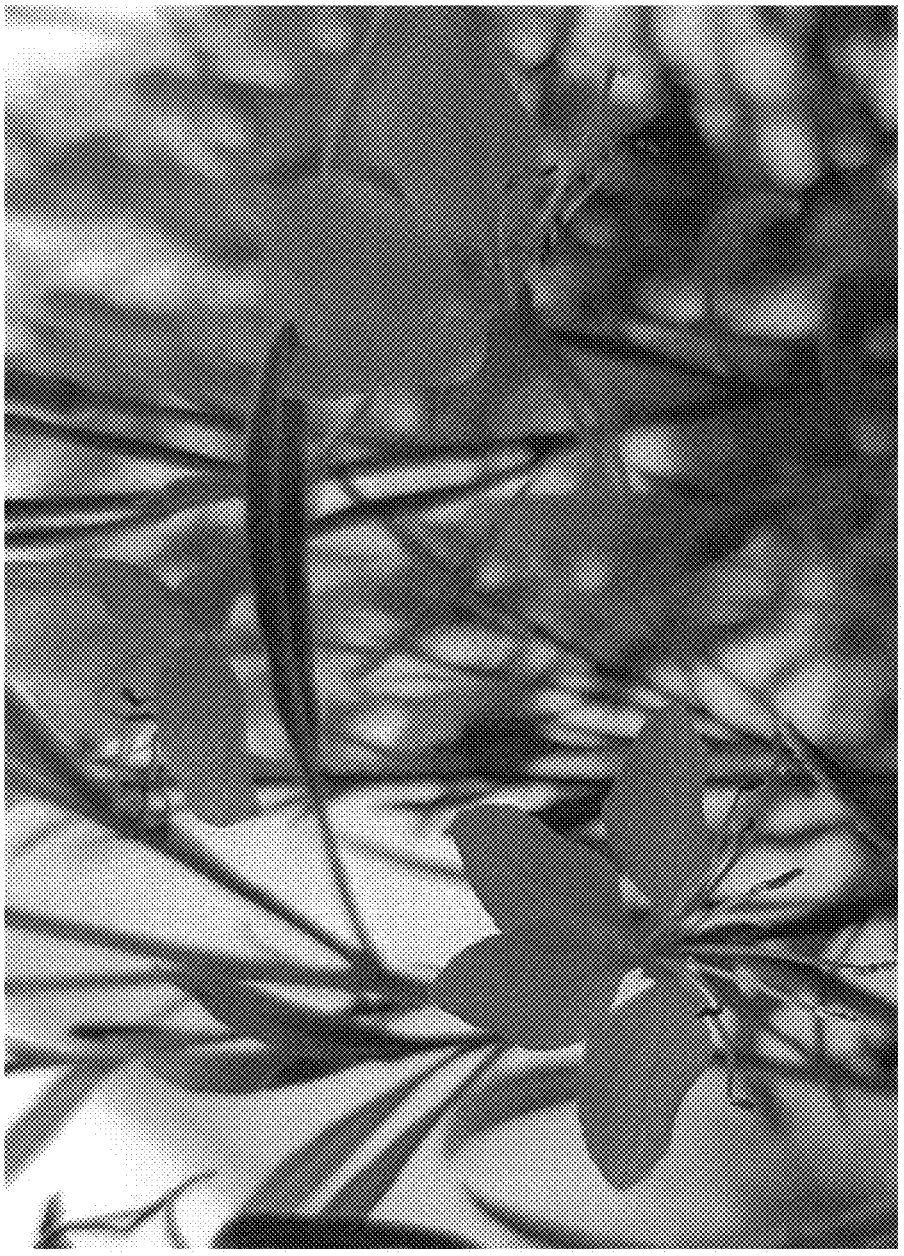

FIG. 2 illustrates in full color typical flowers of 'DGASTEFDR'. Age of the plant photographed is approximately 50 days old in a 12 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DGASTEFDR' plants grown in a nursery in Moshav Mishmar Hashiva, Israel, under natural lighting. Measurements were taken during April 2019. The plants were approximately 50 days old in a 12 cm pot. The growing temperature ranged from 6° C. to 35° C. during the days, 0° C. to 22° C. during the nights. Measurements and numerical values represent averages of typical plant types.

Botanical classification: *Gaura lindheimeri* 'DGASTEFDR'.

PROPAGATION

Time to initiate roots: 14 days at 16-20° C.

Root description: Fibrous, colored near RHS White 155D.

PLANT

Growth habit: Semi-upright, compact.

Pot size of plant described: 12 cm.

Height: 31 cm.

Plant spread: 16 cm.

Growth rate: Medium.

Branching characteristics:

Length of primary lateral branches: 31 cm.

Quantity of primary lateral branches: Average 5.

Characteristics of primary lateral branches:

- *Form*.—Round.
- *Diameter*.—0.35 cm.
- *Color*.—Immature branches: Upper tip: Close to RHS Red-Purple 560B. Below: Close to RHS Green 137B. Mature branches: Close to RHS Green 137C.
- *Texture*.—Slightly pubescent.
- *Strength*.—Strong, somewhat flexible.

Internode length: 1.2 to 1.5 cm.

FOLIAGE

Leaf:

- *Arrangement*.—Alternate, simple.
- *Quantity*.—Approximately 16 to 20 per branch.
- *Average length*.—5.5 cm.
- *Average width*.—1.2 cm.
- *Shape of blade*.—Oblanceolate.
- *Apex*.—Acute.
- *Base*.—Cuneate.
- *Margin*.—Entire.
- *Texture of top surface*.—Scant pubescence.
- *Texture of bottom surface*.—Scant pubescence.
- *Aspect*.—Flat with little undulation at apex.
- *Variegation*.—None.
- *Color*.—Young foliage upper side: RHS Green 137B. Young foliage under side: RHS Green 137C. Mature foliage upper side: RHS Green N137A. Mature foliage under side: RHS Green N137C.
- *Venation*.—Type: Pinnate. Venation Color, Mature Foliage: Upper side: RHS Green 138D. Under side: RHS Yellow-Green 147D. Venation Color, Young Foliage: Upper side: RHS Yellow-Green 147D. Under side: RHS Yellow-Green 147C.
- *Petiole*.—Sessile.

FLOWER

Natural flowering season: Spring through Summer.

Inflorescence type: Single zygomorphic flowers produced on terminal and axillary racemes.

Persistent or self-cleaning: Self-cleaning.

Bud:

- *Length*.—Average 1.5 cm.
- *Diameter*.—0.2 to 0.25 cm.
- *Color*.—Near RHS Red-Purple 60B; tip near RHS Green 138B.

Raceme:

- *Diameter*.—Average 5 cm.
- *Length*.—Average 11 cm.
- *Flowers per raceme*.—8 to 10 (5 open flowers).

Flower size:

- *Diameter*.—Average 3.3 cm.
- *Length*.—Average 1.7 cm.

Corolla/petals:

- *Quantity of petals*.—4.
- *Arrangement*.—Symmetrical whorl.
- *Petal length*.—1.6 cm.
- *Petal width*.—1 cm.
- *Corolla tube length*.—1.2 cm.
- *Corolla tube diameter*.—0.1 cm.
- *Texture*.—Glabrous.
- *Petal apex*.—Obtuse.
- *Petal base*.—Acute.
- *Petal shape*.—Rounded, spatulate.
- *Margin*.—Entire.
- *Aspect*.—Upwardly cupped.

Petal color:

- *When opening*.—Upper surface: Near RHS Red-Purple 63B. Lower surface: Near RHS Red-Purple 63B.
- *Fully opened*.—Upper surface: Near RHS Red-Purple N66C; veins near Red-Purple 63B. Lower surface: ear RHS Red-Purple N66C; veins near Red-Purple 63B.

*Fading*.—Upper surface: Near RHS Red-Purple 65B; veins Red-Purple 63C. Lower surface: Near RHS Red-Purple 65B; veins Red-Purple 63C.

*Conspicuousness of veins*.—Weak to medium.

*Outer corolla tube color*.—Near RHS Red-Purple 61B.

*Inner corolla tube color*.—Near RHS Yellow-Green 144A.

Calyx/sepals:

*Quantity per flower*.—4.

*Shape*.—Linear.

*Length*.—1.5 cm.

*Width*.—0.1 cm.

*Apex*.—Acute.

*Base*.—Truncate.

*Margin*.—Entire.

*Texture*.—Glabrous.

*Aspect*.—Undulating and strongly reflexed back.

*Color*.—Upper Surface: Near RHS Red-Purple 58A; tip Green 138C. Lower Surface: Near RHS Red-Purple 58A; tip Green 138C.

Peduncle:

*Length*.—Average 4 cm.

*Diameter*.—Approximately 0.15 cm.

*Color*.—Near RHS Green 137C.

*Orientation*.—Straight, approximately 15° angle from stem.

*Texture*.—Glabrous.

*Strength*.—Strong.

Pedicel: Not present, directly attached by corolla tube to peduncle.

Fragrance: Not observed.

REPRODUCTIVE ORGANS

Stamens:

*Number*.—8.

*Filament length*.—1.2 cm.

*Filament color*.—Near RHS Red-Purple 63D.

Anthers:

*Shape*.—Linear.

*Length*.—Approximately 0.25 cm.

*Color*.—RHS Red-Purple 59A.

*Pollen*.—Color: Near RHS Yellow 1D. Quantity: Abundant.

Pistil:

*Number*.—1.

*Length*.—1.7 cm.

*Style*.—Length: 1.5 cm. Color: RHS Red-Purple 63D.

*Stigma*.—Shape: 4-lobed. Color: RHS White N155D. Ovary: Color: RHS Red-Purple 61A. Ovary Length: Approximately 0.8 cm. Ovary Diameter: Approximately 0.1 cm. Ovary Shape: Linear.

OTHER CHARACTERISTICS

Seeds and fruits: Not observed to date.

Disease/pest resistance, tolerance or susceptibility: Neither resistance nor susceptibility to diseases or pests has been observed in this variety.

Temperature tolerance: Approximately 0° C. to 38° C.

What is claimed is:

1. A new and distinct cultivar of *Gaura* plant named 'DGASTEFDR' as herein illustrated and described.

* * * * *